US006571795B2

(12) United States Patent
Bourdon

(10) Patent No.: US 6,571,795 B2
(45) Date of Patent: *Jun. 3, 2003

(54) BREATHING AID APPARATUS IN PARTICULAR FOR TREATING SLEEP APNOEA

(75) Inventor: Guy Bourdon, Verrieres le Buisson (FR)

(73) Assignee: Nellcor Puritan Bennett France Developpement (FR)

( * ) Notice: Subject to any disclaimer, the term of this patent is extended or adjusted under 35 U.S.C. 154(b) by 195 days.

This patent is subject to a terminal disclaimer.

(21) Appl. No.: 09/775,424

(22) Filed: Feb. 1, 2001

(65) Prior Publication Data

US 2001/0004894 A1 Jun. 28, 2001

Related U.S. Application Data

(63) Continuation of application No. 08/839,459, filed on Apr. 14, 1997, now Pat. No. 6,283,119, which is a continuation of application No. 08/360,720, filed as application No. PCT/FR93/00547 on Jun. 9, 1993, now abandoned.

(30) Foreign Application Priority Data

Jun. 15, 1992 (FR) .............................................. 92 07184

(51) Int. Cl.⁷ ............................................. A61M 16/00
(52) U.S. Cl. ............................ 128/204.23; 128/204.18; 128/204.21
(58) Field of Search ....................... 128/200.24, 207.22, 128/204.18, 204.21, 204.22, 204.23

(56) References Cited

U.S. PATENT DOCUMENTS

| | | | |
|---|---|---|---|
| 3,267,935 A | | 8/1966 | Andreasen et al. |
| 4,305,400 A | * | 12/1981 | Logan .................... 128/204.18 |
| 4,637,385 A | | 1/1987 | Rusz |
| 5,047,930 A | * | 9/1991 | Martens et al. ........ 364/413.04 |
| 5,107,830 A | | 4/1992 | Younes |
| 5,117,819 A | * | 6/1992 | Servidio et al. ........ 128/204.18 |
| 5,148,802 A | * | 9/1992 | Sanders et al. ......... 128/204.18 |
| 5,199,424 A | * | 4/1993 | Sullivan et al. ........ 128/204.18 |
| 5,239,995 A | * | 8/1993 | Estes et al. ............. 128/204.23 |
| 5,245,995 A | * | 9/1993 | Sullivan et al. ........ 128/204.23 |
| 5,299,118 A | * | 3/1994 | Martens et al. ........ 364/413.05 |
| 5,458,137 A | * | 10/1995 | Axe et al. ............... 128/204.23 |
| 6,283,119 B1 | * | 9/2001 | Bourdon ................ 128/204.23 |

FOREIGN PATENT DOCUMENTS

| | | |
|---|---|---|
| EP | 0 042 321 A1 | 12/1981 |
| FR | 2 663 547 A1 | 12/1991 |
| GB | 2 054 387 A | 2/1981 |

OTHER PUBLICATIONS

French Search Report for relating French Application No. 9211131, dated Jun. 29, 1993.

International Preliminary Examination Report for relating International Application PCT/FR93/00902, dated Jun. 9, 1994.

(List continued on next page.)

Primary Examiner—Weilun Lo
Assistant Examiner—Joseph F. Weiss, Jr.
(74) Attorney, Agent, or Firm—Fulwider Patton Lee & Utecht, LLP

(57) ABSTRACT

A compressor driven by a motor sends to a nasal mask a breathable gas at a low positive relative pressure whereby the motor is controlled to maintain the pressure in the delivery pipe of the compressor substantially equal to a set point, independently of the inspiration and expiration of the patient, a computer receiving on an input a motor speed signal as a parameter representative of the respiratory activity of the patient and analyzing the motor speed variations whereby the computer will increase the pressure set point if necessary or reduces the pressure set point by a predetermined amount depending upon whether there is a hypopnoea or the absence thereof.

20 Claims, 3 Drawing Sheets

OTHER PUBLICATIONS

A first Opposition brief against the relating European Patent 0 662 009 B1, dated Feb. 15, 1999.

Response to Opposition relating to European Patent 0 662 009 B1, dated Oct. 8, 1999.

A second Opposition brief against the relating European Patent 0 662 009 B1, dated Jan. 19, 2000.

Response to second Notice of Opposition for European Patent 0 662 009 B1, dated Apr. 21, 2000.

European Patent Office's decision on the Opposition for European Patent 0 662 009, dated Sep. 27, 2001.

Puritan–Bennett Brochure, Flow–By, Option 50, p. 1–6, dated Oct. 1986.

Puritan–Bennett, 7200 Microprocessor Ventilator Service Manual, Figure 2–1 Electro–Pneumatic System, dated Jun. 1983.

Puritan–Bennett, 7200 Microprocessor Ventilator Operator's Manual, dated Mar. 1986.

The Future Begins . . . with Puritan–Bennett's 7200 Microprocessor Ventilator, dated May 1983.

Conference Proceedings, the New Generation of Mechanical Ventilators, Respiratory Care, Jun. 1987, vol. 32 No. 6, p. 403–418.

Grounds of Decision of Revocation relating to European Appln. No. Ser. No. 95/930565.7—dated Oct. 16, 2001 (with translation).

F. Clergue, M. Bakir & T. Tarakat, "Le respirateur Servo Ventilator 900C," Departement d'anesthesie–reanimation (Pr P. Viars) Groupe hospitalier Pitie, Salpetriere, Paris, p. 417–421, dated 1984.

Siemens News Letter, dated Nov. 1992.

Siemens Technical Brochure of the SV300, dated Mar. 1992.

* cited by examiner

BREATHING AID APPARATUS IN PARTICULAR FOR TREATING SLEEP APNOEA

CROSS REFERENCE TO RELATED APPLICATIONS

This application is a continuation of U.S. application Ser. No. 08/839,459 filed Apr. 14, 1997, now U.S. Pat. No. 6,283,119; which is a continuation of U.S. application Ser. No. 08/360,720 filed Dec. 12, 1994, now abandoned, which is a §371 application claiming priority to PCT/FR93/00547 filed Jun. 9, 1993 and claims priority to foreign application FRANCE 92 07184 filed Jun. 15, 1992.

BACKGROUND OF THE INVENTION

The present invention relates to a breathing aid apparatus, in particular for treating people which are prone to the disease called "sleep apnoea".

Sleep apnoea syndrome (SAS) is the accumulation of signs as well as their consequences due to the periodic interruption of respiration during sleep. The re-establishment of respiration generally only occurs when the person concerned wakes up. This phenomenon can occur several hundred times per night, with interruptions of 10 seconds or more each time.

Three types of apnoea syndrome exist, each corresponding to a particular pathology.

The first type, which is the most common, is obstructive apnoea. It results from an obstruction of the upper respiratory tracts caused by a collapse of the tongue and the palate. The respiratory movements continue, but because of this obstruction, air can neither enter nor leave the lungs.

The second type, which is rarer, is called "central apnoea". It is produced when the respiratory center of the brain no longer controls respiration. In the absence of a signal originating from the brain, the respiratory muscles do not function and air can neither enter nor leave the lungs.

The third type is mixed apnoea which is a combination of the two previous types, the start of the apnoea being of central type.

In the case of obstructive apnoea and mixed apnoea, treatment by continuous positive pressure is the most commonly used. This technique consists of permanently applying, via a nasal mask connected by a pipe to a pressure generating apparatus, a low positive relative pressure in the upper respiratory tracts in order to avoid their obstruction. This pressure prevents the tongue and palate from sticking together. The result is immediate: interrupted respiration is re-established, the lungs receive the oxygen they need and the person sleeps much better.

The optimum value of the pressure corresponds to the minimum allowing the suppression of apnoeas and the oxygen desaturations which result in the blood.

Determination of this optimum pressure is carried out in the laboratory, by subjecting the patient to a polygraph recording, and by progressively raising the level of pressure applied to the patient until the disappearance of respiratory incidents.

The treatment described previously, which consists of applying a constant pressure level to the patient throughout the night, has certain deficiencies.

In fact, the frequency and extent of apnoeas vary during the night according to the stage of sleep the patient is in. Also, they vary over time as a function of the development of the condition of the patient (gain or loss of weight, absorption of alcohol before going to sleep . . . ).

Therefore, the treatment pressure determined by the prescription is not necessarily adequate subsequently. Now, control recordings cannot be carried out regularly, due to their cost and the significant burden on sleep laboratories, connected with the large number of patients to be treated.

In addition, the patient is subjected to an identical pressure all night, whereas depending on the stages of his sleep, a lower pressure may be sufficient, or a higher pressure may be necessary. Now, the lower the average pressure applied during the night is, the better the patient's comfort will be and therefore his acceptance of the treatment, and the more the deleterious effects linked with too high a pressure will be minimised.

SUMMARY OF THE INVENTION

The aim of the present invention is to propose a breathing aid apparatus which allows the treatment to be optimized as a function of the effective needs of the patient at each stage of treatment.

According to the invention, the breathing aid apparatus, in particular for treating sleep apnoea, comprising means of producing a flow of breathable gas under a low positive relative pressure, and means for leading this flow to a respiratory mask, is characterized in that in addition the apparatus comprises means of acquiring a parameter representative of the respiratory activity of the patient, and automatic adjustment means for increasing the pressure applied at least when the representative parameter is indicative of a hypopnoea, and for reducing the applied pressure when the representative parameter is indicative of normal respiration over a predetermined time.

The term "hypopnoea" encompasses the phenomena of the total disappearance of respiration, and can also include certain phenomena of partial disappearance of respiration, due to a partial obstruction of the upper respiratory tracts.

Thanks to the invention, the treatment apparatus is no longer a simple constant pressure generator, but becomes an apparatus capable of detecting hypopnoeas and of adjusting the pressure level in order to suppress the hypopnoeas.

In this way, thanks to the apparatus, each time a hypopnoea is detected, the pressure is increased, preferably by increments, until the hypopnoea ceases. When no hypopnoea has occurred for a defined period of time, the pressure is reduced by a predetermined value.

This process allows hypopnoeas to be put to an end while permanently minimizing the applied pressure.

Preferably, the pressure cannot go below a lower threshold defined by the consultant and set on the apparatus, and of course it cannot exceed the maximum value that the apparatus is capable of delivering, or a maximum value defined by the doctor.

Other characteristics and advantages of the invention will become apparent from the description below, with reference to the non-limitative examples.

DESCRIPTION OF THE PREFERRED EMBODIMENTS

Figure 1:
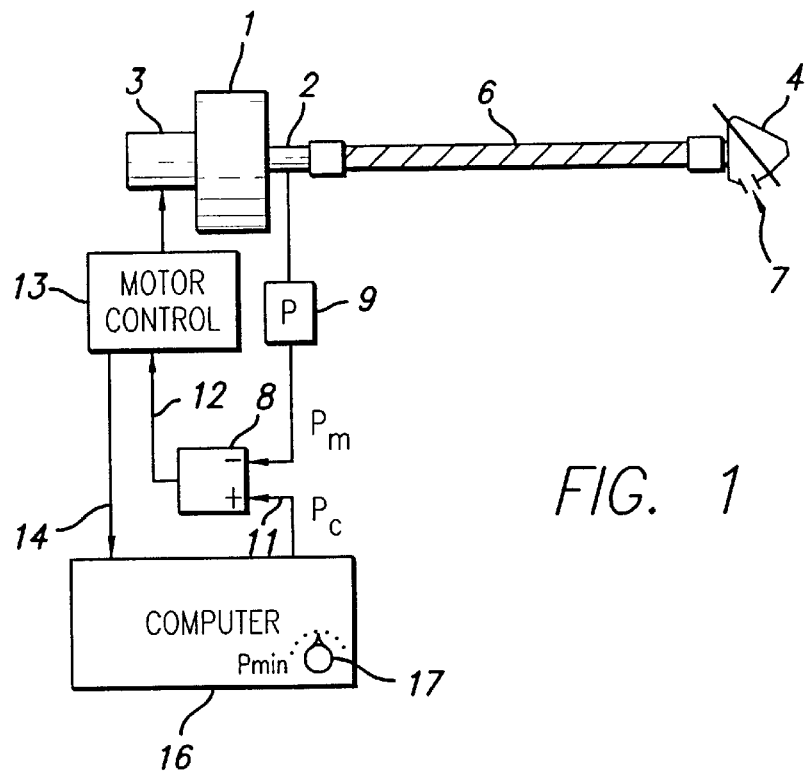
FIG. 1 is a diagram of an apparatus according to the invention.

The apparatus represented in FIG. 1 comprises a compressor 1 capable of producing through its delivery pipe 2 a breathable gas at a positive relative pressure, i.e. measured relative to atmospheric pressure, which depends on the rotational speed of the drive motor 3. In a non-represented manner, the compressor 1 is of a type which produces the positive relative pressure by a turbine for propelling breathable gas. The delivery pipe 2 is connected to a nasal mask 4 by a flexible tube 6. The nasal mask 4 is intended to be applied to the patient's face, for example by means of a strap. The mask 4 includes an opening 7 allowing the patient to expire despite the flow in the opposite direction coming from the compressor 1.

A comparator 8 permanently compares the pressure $P_m$ detected in the delivery pipe 2 of the compressor 1 by a pressure detector 9 with a pressure set point $P_c$ applied to the other input 11 of the comparator 8. As a function of the result of the comparison, the comparator 8 supplies at its output 12 a signal applied to a motor control device 13 to reduce the rotational speed of the motor 3 when the pressure measured by the detector 9 is greater than the pressure set point, and to increase the rotational speed of the motor 3 and therefore the pressure at the delivery pipe 2 when the pressure measured by the detector 9 is lower than the pressure set point.

In this way, the pressure at the delivery pipe 2 and therefore in the nasal mask 4, is approximately the same during the inspiration phases and during the expiration phases of the patient.

During the inspiration phases, a relative low pressure tends to be created at the delivery pipe 2 of the compressor 1, and maintaining the pressure at the set point value requires an increase in the rotational speed of the motor 3.

On the other hand, during the expiration phases of the patient, an excess pressure tends to be created at the delivery pipe 2, and maintaining the pressure at the set point value requires a decrease in the rotational speed of the motor 3.

Consequently, when the respiration of the patient is normal, the rotational speed of the motor 3 follows a periodical curve.

According to the embodiment in FIG. 1, a signal representative of the rotational speed of the motor 3 is applied by the control device 13 to the input 14 of a computer 16 whose function is to analyze the curve of the speed of the motor 3 as a parameter representative of the respiratory activity of the patient, and to modify the pressure set point $P_c$ applied to the input 11 of the comparator 8 as a function of the result of this analysis.

In a general fashion, when the analysis of the curve of the rotational speed of the motor reveals a hypopnoea situation, the computer 16 increases the pressure set point.

On the other hand, if the analysis of the curve of the speed of the motor reveals an absence of hypopnoea for a certain predetermined period of time, the computer reduces by a predetermined amount the pressure set point.

The computer 16 is connected to a manual control 17 allowing the minimum pressure set point $P_{min}$ authorized by the doctor for each patient to be adjusted.

Figure 2:
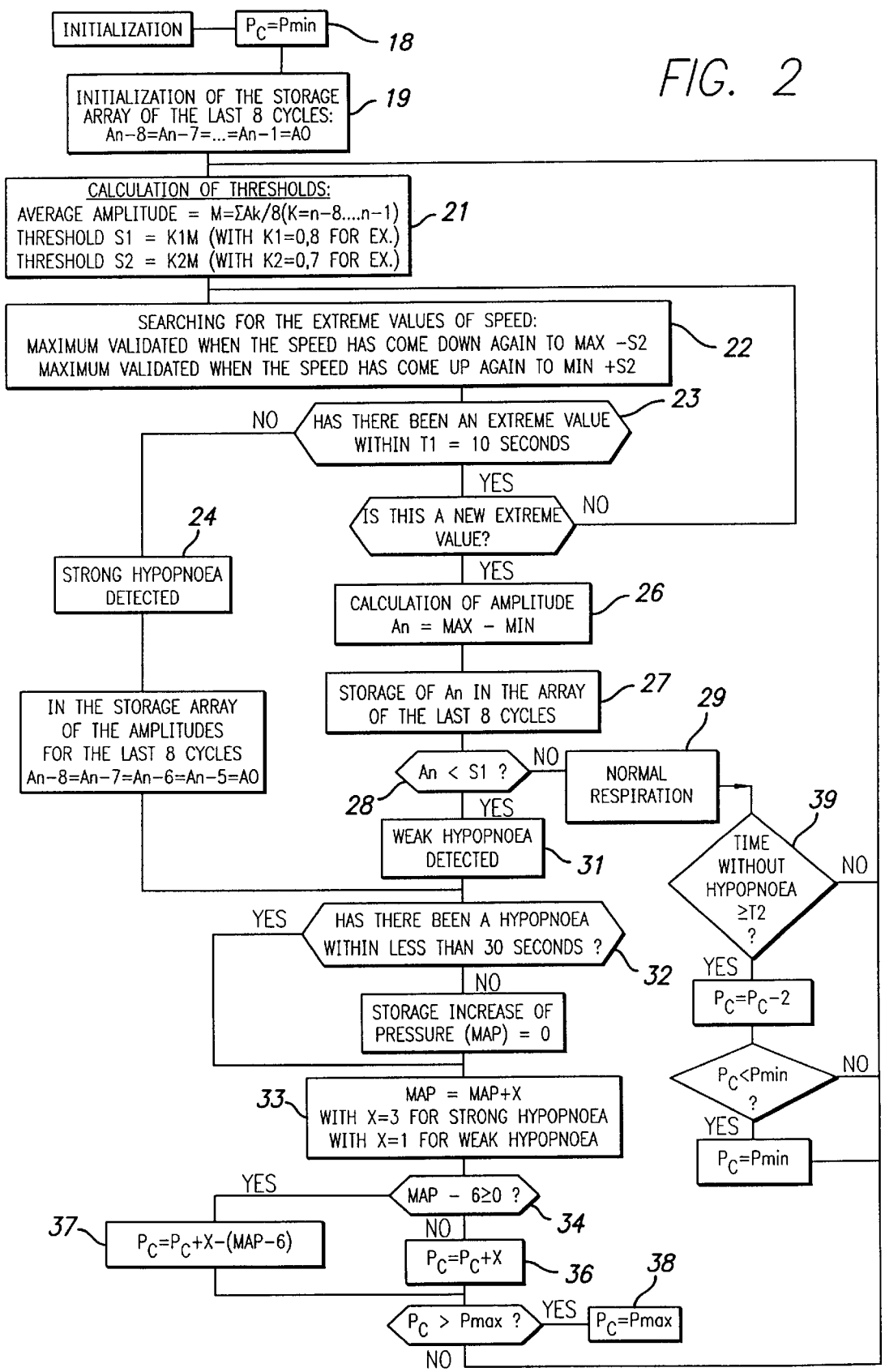
FIG. 2 is a flow chart for the operation of the computer of FIG. 1.

There will now be described with reference to FIG. 2, the flow chart according to which, essentially, the computer 16 is programmed.

In what follows, by "hypopnoea" is meant the symptom consisting either of an abnormal lowering (for example by 50%) of the respiratory activity, or the symptom of total apnoea consisting of the complete disappearance of respiratory activity.

At the start, the pressure set point $P_c$ is chosen to be equal to $P_{min}$, i.e. the minimum pressure set point chosen using the manual control 17 (stage 18).

In stage 19, the values An–8, An–7, . . . , An–1 of the amplitude of the motor speed variation during the eight respiratory cycles before the one which is currently being analyzed, are arbitrarily set equal to a value A0 which is relatively low.

Then, in stage 21, the average of the amplitudes of the eight previous cycles (average M) is calculated and two thresholds S1 and S2 are calculated with for example:

S1=0.8 M

S2=0.7 M

In stage 22, the extreme values of the rotational speed of the motor are sought.

In order to do this, the rotational speed of the motor at each execution cycle of the program is stored in memory. A maximum or minimum is only validated if the speed has then varied sufficiently so as to be back from this maximum or minimum by a value at least equal to threshold S2.

In other words, as the threshold S2 is greater than half of the average of the previous amplitudes, a given extreme value will only be processed if the speed again then reaches a value beyond that of the average of the speeds. In particular, if respiration stops (total apnoea), the speed of the motor assumes its average value and the previous extreme value is not validated. More generally, if an amplitude lower than threshold S2 tends to become established, it will no longer be possible to validate the extreme values.

After a period of time T1 equal for example to 10 seconds, this is detected in the following test 23. In the absence of an extreme value for 10 seconds, one follows the path "detection of strong hypopnoea" 24 of the flow chart, in which the four amplitudes An–8 . . . An–5 which are the oldest values still in memory are reduced to the relatively low value of A0. The aim of this is to reduce the thresholds S1 and S2 for the next calculation cycle so as to make the resumption of respiratory activity easier to detect.

Returning to test 23, if an extreme value was found within the 10 previous seconds and if this extreme value is the same as that already processed during the previous calculation cycle, one returns to stage 23 in order to search for extreme values.

If, on the other hand, the extreme value is new, one passes via stage 26 for calculating the new amplitude An, then, stage 27, storing in memory the amplitude An while simultaneously deleting the oldest amplitude in memory An–8.

In stage 28, the newly-calculated amplitude An is compared with the largest S1 of the two thresholds.

If the newly-calculated amplitude An is greater than threshold S1, one follows normal respiration path 29 which will be described further on.

In the opposite case, i.e. if the amplitude is between thresholds S1 and S2, it is considered that a weak hypopnoea 31 exists.

Whether strong hypopnoea 24 or weak hypopnoea 31 has been recorded, a test 32 is carried out in order to determine whether there was already a hypopnoea during the previous 30 seconds. If the result is negative a number MAP is reset to zero. MAP corresponds to the total increase in pressure in the previous 30 seconds.

If, on the other hand, there was hypopnoea during the previous 30 seconds, the MAP number is not reset to zero.

The following stage 33 consists of adding a relatively high increment to the MAP number if strong hypopnoea was detected, and a relatively low increment if weak hypopnoea was detected. Then, in stage 34, a test is carried out to establish whether the MAP number is greater than 6 cm of water (6 $hP_a$). If the result is negative, stage 36, an increment X, being high or low depending on the strength of the hypopnoea, is added to the pressure set point $P_c$. If, on the other hand, MAP exceeds 6, the pressure set point $P_c$ is only increased to the extent that the total increase in the previous 30 seconds is equal to 6 (stage 37).

The aim of this is to avoid increasing the pressure excessively to treat a single hypopnoea: if an increase of more than 6 cm of water is necessary to treat a hypopnoea, it is because there is some anomaly and it would be better to wake the patient up.

Then, the new pressure set point is applied to the comparator 8 in FIG. 1 on the condition that it does not exceed the maximum pressure set point $P_{max}$. If the pressure $P_c$ exceeds $P_{max}$, the set point applied to the comparator 8 is equal to $P_{max}$ (stage 38). One is then returned to stage 21 in which the thresholds are calculated. If the strong or weak hypopnoea which was detected during the previous cycle is still not alleviated, the pressure set point will be increased by a new increment and so on until the total pressure increase MAP within 30 seconds reaches 6 cm of water or until the hypopnoea is alleviated.

In this way, the amplitude is compared to two different thresholds, one to detect strong hypopnoeas, including the total hypopnoeas, and to apply a relatively swift increase in the pressure set point, the other to detect weak hypopnoeas, resulting from a partial obstruction of the upper respiratory tract, and to apply a clearly milder increase in pressure.

One of the important features of the invention consists of analyzing the parameter representative of respiratory activity (the speed of the motor 3) not by comparison with absolute thresholds, but by comparison with the respiratory activity which has just preceded the respiratory anomaly. In fact, it has been noted that respiratory activity varies greatly during sleep, to the extent that an activity which would be considered normal during a certain phase of sleep can correspond to a hypopnoea in another phase of sleep.

Returning to path 29 of the flow chart, this leads to a test 39 for determining whether a time T has passed without detecting a hypopnoea. If the result is negative, one returns to stage 21 in which the thresholds are calculated.

If, on the other hand, a time T2, for example equal to 30 minutes, has passed without a hypopnoea, the pressure set point is reduced by, for example, 2 cm of water. In this way one provides an opportunity to bring the pressure applied to the patient to a lower value if this is possible.

However, if the new pressure set point thus became lower than the minimum pressure as set with the manual control 17 of FIG. 1, the pressure set point is simply reset equal to the minimum pressure set. Then, once again, one is returned to stage 21 in which the thresholds are calculated.

Figure 3:
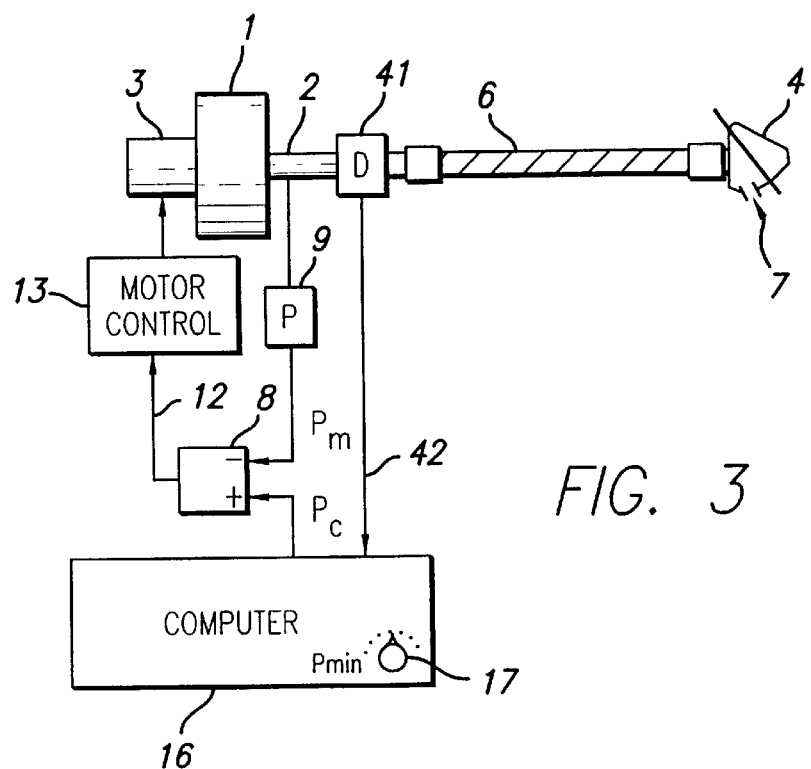
FIGS. 3 and 4 are diagrams similar to FIG. 1 but relating to two other embodiments.

In the example represented in FIG. 3, which will only be described with regard to its differences relative to that of FIG. 1, a flow rate detector 41 is placed on the delivery pipe 2 of the compressor 1 whose signal is sent to an input 42 of the computer. On the other hand the computer no longer receives a signal corresponding to the rotational speed of the motor. It is now the flow rate signal provided by the detector 41 which provides the computer with the parameter representative of the respiratory activity. When the patient inspires, the flow rate detector 41 reveals a higher flow rate than when the patient expires. In other words, the variations in flow rate work in the opposite sense to those of the speed of the motor 3. Apart from that, nothing is changed, and the flow chart of FIG. 2 is valid for the embodiment of FIG. 3, with the exception that in stage 22 in which the extreme values are sought, the word "speed" must be replaced by the words "flow rate".

Figure 4:
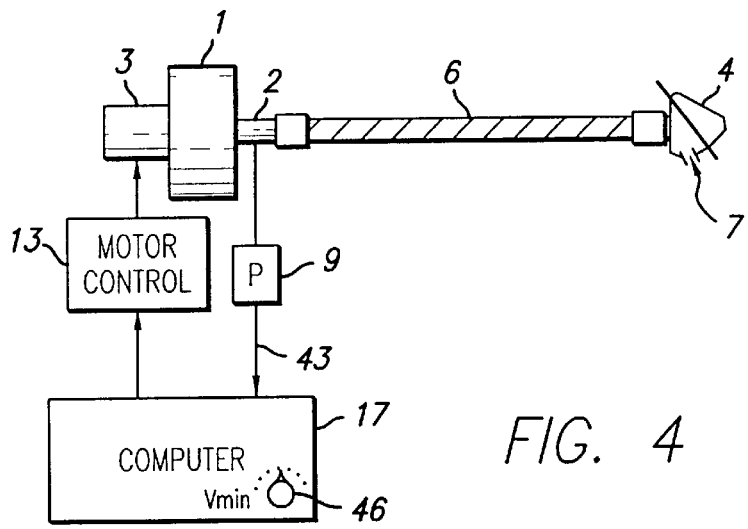

The example of FIG. 4 corresponds to a simplified version.

In this example, which will only be described with regard to its differences relative to that of FIG. 1, there is no pressure regulation at the delivery pipe 2, i.e., apart from situations of apnoea or hypopnoea, the motor 3 rotates at the same speed whether the patient inspires or expires. The pressure at the delivery pipe 2 is therefore relatively low when the patient inspires and relatively high when he expires. Therefore, the pressure at the delivery pipe 2 constitutes a parameter representative of the respiratory activity and it is, as such, detected by the pressure sensor 9. The computer 16, which receives the pressure signal 9 on an input 43, analyzes the pressure curve and provides the control device 13 of the motor 3 with a signal for increasing the speed of the motor 3 when the variations in pressure indicate a situation of hypopnoea, and for decreasing the speed of the motor 3 when any situation of hypopnoea has not been alleviated within a predetermined period of time, for example 30 minutes.

Figure 5:
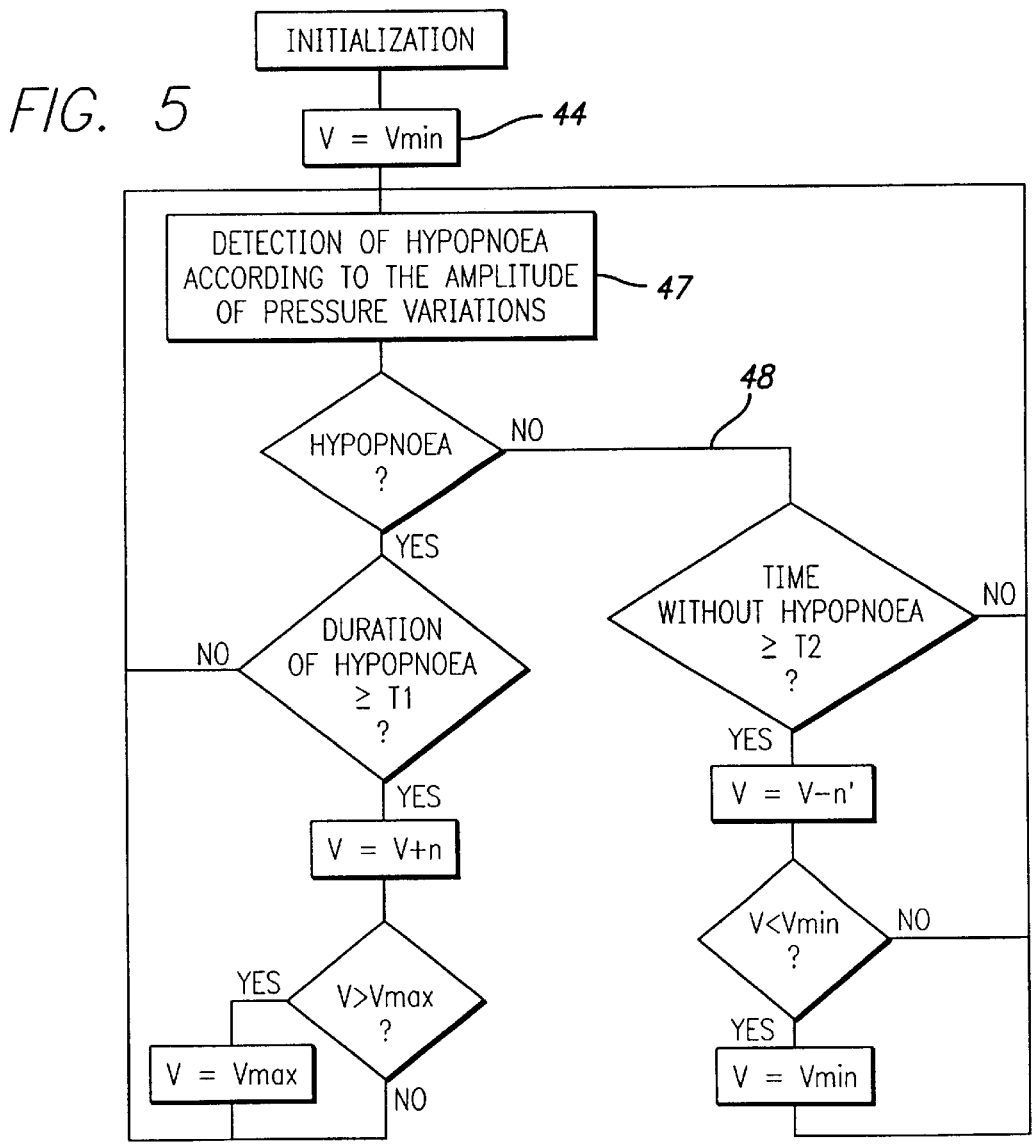
FIG. 5 is a flow chart of the operation of the computer of the embodiment of FIG. 4.

FIG. 5 represents a schematic flow chart according to which the computer 17 of FIG. 4 can be programmed.

At the start, the speed V of the motor is adjusted to a value $V_{min}$ (stage 44) set with a manual control 46 (FIG. 4).

Then one passes to stage 47 in which hypopnoeas are detected according to the amplitude of the variations in pressure. This stage can correspond to stages 21 and 22 of FIG. 2, except that it is then applied to the pressure instead of being applied to the speed of the motor. In the absence of hypopnoea, one passes via path 48 in which the speed of the motor is reduced by a predetermined value n' if a time T2, for example 30 minutes, has passed without hypopnoea, without however lowering the speed to a value which is less than the set speed $V_{min}$.

In the case of a hypopnoea being detected during a period of time greater than or equal to a value $T_1$ of for example 10 seconds, the speed V is incremented by a predetermined value n, without however allowing the speed to exceed a value $V_{max}$.

Consequently, in this simplified example, only a single degree of intensity of hypopnoea is distinguished and when the hypopnoea is detected, one and the same mode of action is envisaged in every case, i.e. an incrementation of the speed of the motor according to one predetermined step and one only.

Of course, the invention is not limited to the examples as described and represented.

In the computers of the embodiments according to FIGS. 1 and 3 a program could be envisaged which distinguishes only one type of hypopnoea, or on the other hand, the embodiment according to FIG. 4 could be equipped with a program which processes in a different way the weak hypopnoeas and the strong hypopnoeas as was described with reference to FIG. 2.

While particular forms of the invention have been illustrated and described, it will also be apparent to those skilled in the art that various modifications can be made without departing from the spirit and scope of the invention. Accordingly, it is not intended that the invention be limited, except as by the appended claims.

What is claimed is:

1. An apparatus for controlling the positive pressure of breathable gas to the airway of a patient, comprising:
   means for producing breathable gas at positive pressure;
   means for controlling the positive pressure of the breathable gas;
   means for determining an amplitude of variation of the means for controlling the positive pressure of the breathable gas;
   means for detecting the presence of a hypopnoea as a function of the amplitude of variation; and
   means for increasing the positive pressure of the breathable gas when the means for detecting reveals the presence of a hypopnoea.

2. The apparatus of claim 1, further including means for decreasing the positive pressure of the breathable gas when the means for detecting reveals the absence of a hypopnoea.

3. The apparatus of claim 2, wherein the means for producing breathable gas at positive pressure includes a drive motor operably connected to a compressor, and wherein the means for controlling the positive pressure includes a motor control operably connected to the drive motor.

4. The apparatus of claim 3, wherein the means for controlling the positive pressure further includes a pressure detector and a comparator operably connected to the motor control.

5. The apparatus of claim 4, wherein the means for determining an amplitude of variation utilizes a signal from the motor control indicative of the rotational speed of the drive motor.

6. The apparatus of claim 1, wherein the means for detecting the presence of a hypopnoea includes means for comparing a present amplitude of variation with a threshold value calculated from at least one previous amplitude of variation, wherein the means for increasing the positive pressure increases the pressure of the breathable gas when the present amplitude of variation is below the threshold value.

7. The apparatus of claim 6, wherein means for detecting the presence of a hypopnoea further includes means for calculating the threshold value from an average of about eight previous amplitudes of variation.

8. The apparatus of claim 1, wherein the means for detecting the presence of a hypopnoea includes means for comparing the amplitude of variation with a first threshold for a strong hypopnoea and a second threshold for a weak hypopnoea, wherein the means for increasing the positive pressure increases the pressure of the breathable gas by a first incremental adjustment when the amplitude of variation is greater than the first threshold for a strong hypopnoea, and by a second incremental adjustment when the amplitude of variation is between the first and second thresholds, such that the first incremental adjustment is greater than the second incremental adjustment.

9. An apparatus for the treatment of sleep apnoea, comprising:
   a compressor configured to produce breathable gas at positive pressure;
   a drive motor operably connected to the compressor;
   a pressure detector in fluid communication with an outlet of the compressor;
   a comparator having a first input, a second input and an output, wherein the pressure detector generates a pressure signal connected to the first input;
   a motor control operably connected to the drive motor, the motor control configured to generate a drive motor rotational speed signal, wherein the motor control accepts the output of the comparator; and
   a computer configured to accept the drive motor rotational speed signal, the computer further configured to calculate an amplitude of variation based on the drive motor rotational speed signal and to detect the presence of a hypopnoea, wherein the computer is configured to generate a pressure set point signal connected to the second input to the comparator, such that the set point is calculated to increase the positive pressure of the breathable gas when the amplitude of variation is indicative of a hypopnoea.

10. The apparatus of claim 9, wherein the computer is further configured to generate the pressure set point signal so as to decrease the positive pressure of the breathable gas when the amplitude of variation is indicative of the absence of a hypopnoea.

11. The apparatus of claim 10, wherein the computer is further configured to compare the amplitude of variation with a threshold value, wherein the computer increases the pressure set point when the amplitude of variation is lower than the threshold value.

12. The apparatus of claim 11, wherein the computer is further configured to calculate the threshold value from an average of about eight previous amplitudes of variation.

13. The apparatus of claim 12, wherein the computer is further configured to increase the pressure set point when the amplitude of variation remains below the threshold value for a predetermined period of time.

14. The apparatus of claim 9, wherein the computer is further configured to compare the amplitude of variation with a first threshold for a strong hypopnoea and a second threshold for a weak hypopnoea, wherein the computer increases the pressure set point by a first incremental adjustment when the amplitude of variation is greater than the first threshold for strong hypopnoea, and by a second incremental adjustment when the amplitude is between the first and second thresholds, such that the first incremental adjustment is greater than the second incremental adjustment.

15. A method for controlling the positive pressure of breathable gas to the airway of a patient, comprising:
   producing breathable gas at positive pressure;
   providing a controller to adjust the positive pressure of the breathable gas;
   determining an amplitude of variation as a function of a signal from the controller; and
   increasing the positive pressure of the breathable gas when the amplitude of variation reveals a hypopnoea.

16. The method of claim 15, further including reducing the positive pressure of the breathable gas when the amplitude of variation reveals the absence of a hypopnoea.

17. The method of claim 16, further including comparing the amplitude of variation with a threshold value, and increasing the positive pressure of the breathable gas when the amplitude of variation is lower than the threshold value.

18. The method of claim 17, further including calculating the threshold value from an average of about eight previous amplitudes of variation.

19. The method of claim 18, further including increasing the pressure set point when the amplitude of variation remains below the threshold value for a predetermined period of time.

20. The method of claim 15, further including comparing the amplitude of variation with a first threshold for a strong hypopnoea and a second threshold for a weak hypopnoea, and increasing the positive pressure of the breathable gas by a first incremental adjustment when the amplitude of variation is greater than the first threshold for strong hypopnoea, and by a second incremental adjustment when the amplitude of variation is between the first and second thresholds, such that the first incremental adjustment is greater than the second incremental adjustment.

* * * * *